United States Patent
Guliashvili et al.

(10) Patent No.: US 12,121,879 B2
(45) Date of Patent: Oct. 22, 2024

(54) CROSSLINKED POLYSACCHARIDE BASED ABSORBENTS FOR REMOVAL OF ANTI-A AND/OR ANTI-B ANTIBODIES FROM HUMAN PLASMA AND WHOLE BLOOD

(71) Applicant: CytoSorbents Corporation, Monmouth Junction, NJ (US)

(72) Inventors: Tamaz Guliashvili, Monmouth Junction, NJ (US); Maryann Gruda, Monmouth Junction, NJ (US); Thomas Golobish, Monmouth Junction, NJ (US); David James, Monmouth Junction, NJ (US); Karl-Gustav Ruggeberg, Monmouth Junction, NJ (US); Pamela O'Sullivan, Monmouth Junction, NJ (US); Sarah Patterson, Monmouth Junction, NJ (US)

(73) Assignee: CytoSorbents, Inc., Princeton, NJ (US)

( * ) Notice: Subject to any disclaimer, the term of this patent is extended or adjusted under 35 U.S.C. 154(b) by 735 days.

(21) Appl. No.: 17/298,968

(22) PCT Filed: Dec. 2, 2019

(86) PCT No.: PCT/US2019/063934
§ 371 (c)(1),
(2) Date: Jun. 2, 2021

(87) PCT Pub. No.: WO2020/154038
PCT Pub. Date: Jul. 30, 2020

(65) Prior Publication Data
US 2022/0032271 A1 Feb. 3, 2022

Related U.S. Application Data

(60) Provisional application No. 62/775,476, filed on Dec. 5, 2018.

(51) Int. Cl.
| | | |
|---|---|---|
| *B01J 20/32* | (2006.01) | |
| *B01D 15/38* | (2006.01) | |
| *B01J 20/28* | (2006.01) | |
| *C07K 1/22* | (2006.01) | |
| *C07K 16/06* | (2006.01) | |

(52) U.S. Cl.
CPC ...... *B01J 20/3274* (2013.01); *B01D 15/3809* (2013.01); *B01J 20/28019* (2013.01); *B01J 20/28078* (2013.01); *B01J 20/3212* (2013.01); *C07K 1/22* (2013.01); *C07K 16/065* (2013.01)

(58) Field of Classification Search
CPC ............ B01D 15/3809; B01J 20/28004; B01J 20/28019; B01J 20/28078; B01J 20/3212; B01J 20/3219; B01J 20/3274; C07K 1/22; C07K 16/06; C07K 16/065; C07K 16/34; G01N 33/80
See application file for complete search history.

(56) References Cited

U.S. PATENT DOCUMENTS

| | | |
|---|---|---|
| 2014/0284274 A1 | 9/2014 | Nilsson |
| 2016/0168229 A1 | 6/2016 | Paolantonacci et al. |
| 2017/0066839 A1 | 3/2017 | Bian et al. |
| 2018/0345249 A1 | 12/2018 | Bastide et al. |

FOREIGN PATENT DOCUMENTS

| | | |
|---|---|---|
| CN | 105358228 A | 2/2016 |
| CN | 106802352 A | 6/2017 |
| CN | 106995496 A | 8/2017 |
| EP | 3141558 A1 | 3/2017 |
| JP | 2017-053846 A | 3/2017 |
| TW | 201618798 A | 6/2016 |
| WO | WO 2016/177967 A1 | 11/2016 |

OTHER PUBLICATIONS

Song et al.; "Separation of Blood Group Antigen A/B by Immunomagnetic Separation and Utilization of the Adsorption Blood Group A/B Antibodies"; Progress in Modern Biomedicine; vol. 18 No. 14; Jun. 2018; p. 2617-2622 (Abstract Only).
International Patent Application No. PCT/US2019/063934; Int'l Preliminary Report on Patentability; dated Jun. 17, 2021; 6 pages.
International Patent Application No. PCT/US2019/063934; Int'l Search Report and the Written Opinion; dated Jun. 30, 2020; 16 pages.
Aoi et al.; "Importance of pH Homeostasis in Metabolic Health and Diseases: Crucial Role of Membrane Proton Transport"; Biomedical Research Int'l; vol. 2014; ID 598986; Sep. 2014; 8 pages.
Hout et al.; "Specific Removal of Anti-A and Anti-B Antibodies by Using Modified Dialysis Filters"; ASAIO Journal; vol. 46; 2000; p. 702-706.
European Patent Application No. 19911139.4; Extend Search Report; dated Sep. 8, 2022; 7 pages.
Barrett et al.; "The Determination of Pore Volume and Area Distributions in Porous Substances. I. Computations from Nitrogen Isotherms"; The Volume and Area Distributions in Porous Substances; vol. 73; Jan. 1951; p. 373-380.
Kenneth Singh; "The use of nitrogen adsorption for the characterisation of porous materials"; Colloids and Surfaces—A: Physicochemical and Engineering Aspects; No. 187-188; 2001; p. 3-9.

*Primary Examiner* — Brian A McCaig
(74) *Attorney, Agent, or Firm* — BakerHostetler

(57) ABSTRACT

The invention concerns polymeric media based on modified natural polysaccharides for removing one or both of Anti-A Antibodies and Anti-B Antibodies from human blood or plasma, the media comprising one or both of (i) a polymeric solid support with a blood group A Antigen ligand attached to the solid support at a ligand loading between 1-5 mg/mL of solid support, and wherein the media is stable under physiological pH conditions, and (ii) a polymeric solid support with a blood group B Antigen ligand attached to the solid support at a ligand loading between 1-5 mg/mL of solid support, and wherein the media is stable under physiological pH conditions.

12 Claims, No Drawings

CROSSLINKED POLYSACCHARIDE BASED ABSORBENTS FOR REMOVAL OF ANTI-A AND/OR ANTI-B ANTIBODIES FROM HUMAN PLASMA AND WHOLE BLOOD

CROSS-REFERENCE TO RELATED APPLICATIONS

The present application is the National Stage Application of International Patent Application No. PCT/US2019/063934, filed Dec. 2, 2019, which claims priority to U.S. Patent Application No. 62/775,476, filed Dec. 5, 2018, the disclosures of which is are incorporated by reference in their entireties.

GOVERNMENT RIGHTS

This invention was made with government support of under Contract No. W81XWH-17-C-0053 awarded by the U.S. Army Medical Research and Materiel Command. The government has certain rights in the invention.

TECHNICAL FIELD

The present invention relates to the field of bioconjugation of natural or synthetic compounds to form a novel complex having the combined properties of its individual components and in particular having enhanced properties over the individual components. Crosslinking and modifying agents can be applied to couple compounds to solid supports.

BACKGROUND

Antibodies in blood or plasma define four types of blood—A, B, AB and O. The characterization is determined by the hereditary presence or absence of the antigens A and B. Antibodies can cross-react with RBC antigens that are different to those present on the individual's own RBCs. The cross-reaction can be fatal and, as such, is important in transfusions.

Currently some commercially available products for the reduction of Anti-A and Anti-B Antibodies from human plasma/blood include Glycobar-A and Glycobar-B (Elicityl, France), Glycosorb-ABO device (Glycorex Transplantation AB, Sweden). Glycosorb® ABO (Glycorex Transplantation, Sweden) and Biosynsorb columns (no longer available) contain the tri-saccharide terminals of the A and B antigens attached to beads were used clinically to reduce anti-A and anti-B antibodies from organs for ABO incompatible transplantation (Genberg H, G Kumlien L Wennberg, G Tyden. The efficacy of antigen-specific immunoadsorption and rebound of anti-A/B antibodies in ABO-incompatible kidney transplantation. Nephol Dial Transplant. 2011. 2394-2400, hereinafter "Genberg 2011"). The Glycosorb® ABO device is capable of removing up to 30% of the A/B IgM and 20% A/B IgG levels with a single pass (Kannabhiran D, Everly M J, Walker-McDermott J K, Tiongko S, Friedlander R, Putheti P, Sharma V, Dadhania D. Changes in IgG subclasses of donor specific anti-HLA antibodies following bortezomib-based therapy for antibody mediated rejection. Clinical Transplants 2012:229-235] PMID:23721027, hereinafter "Kannabhiran 2012"). Also, recently filed US patent application US2017/0066839 A1 (Merck Patent GmbH, Germany) describes Anti-A and Anti-B antibody removal based on novel affinity chromatography media.

All above mentioned commercial products are based on natural (cellulose) or synthetic polymer (Polyacrylates) material coupled with appropriate blood group antigen A or blood group antigen B type ligands.

There is a need for an improved method to remove antigens A and B to provide a universally donatable plasma or expand the compatibility of donated whole blood.

SUMMARY

In some embodiments, the invention concerns polymeric media based on modified natural polysaccharides for removing one or both of Anti-A Antibodies and Anti-B Antibodies from a Human Plasma, the media comprising one or both of
(i) a polymeric solid support with a blood group A Antigen ligand attached to the solid support at a ligand loading between 1-5 mg/mL of solid support, and wherein the media is stable under physiological pH conditions, and
(ii) a polymeric solid support with a blood group B Antigen ligand attached to the solid support at a ligand loading between 1-5 mg/mL of solid support, and wherein the media is stable under physiological pH conditions. The A Antigen ligand and B Antigen ligands can be on the same or separate supports.

In certain embodiments, the blood group A Antigen ligand is Anti-A-O—$NH_2$ or Anti-A-S—$NH_2$. In other embodiments, the blood group B Antigen ligand is Anti-B-O—$NH_2$ or Anti-B-S—$NH_2$.

The polymeric media may comprise blood group A Antigen ligand attached to a first polymeric solid support and blood group B Antigen ligand attached to a second solid support. Alternately, both antigens may be attached to the same support.

Any suitable material may be used as a solid support. These materials include those comprising at least one of cellulose, dextran, starch, agarose, and chitosan. Some solid supports comprise a beaded form of functional polysaccharide with a bead size range of 45-1,000 um. And pore size ranging from non-porous to 1-20,000 angstrom pore diameter. In some embodiments the bead size is 45 to 800 um. Certain solid supports are functionalized with $NaIO_4$ oxidation followed by secondary crosslinking with appropriate di, tri or polyamines.

In some embodiments, the crosslinked polysaccharide based beaded material is functionalized with natural or synthetic compounds including peptides, proteins, sugars, polysaccharides, nucleotides, oligonucleotides, lipids and drugs.

In certain embodiments, the solid supports are stabilized toward degradation and made stable under wide range of pH (1-14) of the media with partial crosslinking with a di, tri, tetra or polyfunctional primary or secondary amines. One preferred trifunctional amine is tris(2-aminoethyl)amine (TREN).

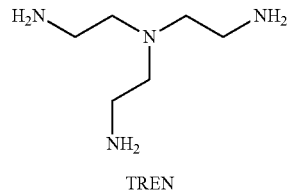

TREN

In some embodiments, the solid support contains partially unreacted aldehyde groups (after $NaIO_4$ oxidation and secondary crosslinking. Such groups may be used for coupling of various amino group containing ligands such as Anti A and Anti B blood group antigen ligands described herein.

DETAILED DESCRIPTION OF ILLUSTRATIVE EMBODIMENTS

Present invention relates to specific functionalization of crosslinked polysaccharide based beaded material (Dextran, Cellulose, etc.) with natural or synthetic compounds Exemplary, but not inclusive, compounds are peptides and proteins, sugars and polysaccharides, nucleotides and oligonucleotides, lipids and drugs. Presentation of complex ligands is a critical factor for recognition and or adsorption of large molecules such as immunoglobulins, lipopolysaccharide and microvesicles, from bodily fluids and other complex solutions. Bioconjugation by unfavorable means to flexible or solid supports can cause loss of ligand activity. Ligand activity depends on the support matrix chosen, linker, ligand density, functionalization conditions and other factors. Proper selection of the carrier or solid support matrix is of decisive importance for the successful application of stereospecific adsorption. In addition, the carrier must have the proper characteristics for the application such as: porosity (porous or nonporous), stability of the ligand attachment; dimensional stability, i.e. the retention of physical shape following changes in pressure, temperature and media; and resistance to microbial attack.

Although techniques for covalent attachments of biological ligands to solid surfaces are well-known in the art, these methods do not work for all ligands. Recognition of polysaccharide ligands, for example but not exclusively, are sensitive to features of presentation such as spacing and orientation of the carbohydrates, linker length and flexibility, and ligand density. An example of Ligand structures sensitive to conditions used during immobilization to the cross-linked polysaccharide-based beads are shown in scheme 1.

These functional tetrasaccharides (tetraoses) are provided by Glycobar (France based company) and represent blood group A and B antigen tetra-saccharides with linker arms that approximate the length of the native hexa-saccharides found on the surface of erythrocytes. An individual's blood type is determined by the ABO antigen system that is derived from specific A and B carbohydrate structures attached to glycolipids on the surface of red blood cells. Individuals develop anti-A or Anti-B immunoglobulins to the blood groups they do not possess, which if transfused to a can hemolyze a mismatched transfusion recipients' RBCs. Individuals with type AB plasma do not develop antibodies to either the A or B antigens, therefore type AB plasma can be transfused to individuals of any ABO blood type. Type AB plasma is in limited supply; therefore, it is desirable to remove anti-A and anti-B antibodies from plasma and blood from A, B and O donors. Optimally, the device must be biocompatible so that it does not cause hemolysis, or clotting or fouling, and specific so that anti-A and anti-B blood group antibodies are efficiently removed from blood and plasma, while beneficial substances such as coagulation factors and albumin are retained. Such a device would be beneficial as it would simplify transfusion logistics, reduce safeguarding costs, and eliminate errors caused by ABO incompatibility.

Scheme 1 shows functionalized Blood Groups A and B antigen tetra-saccharides with linker arm and $NH_2$ functionality.

Blood group A antigen tetra-saccharides with linker arm and $NH_2$ functionality:

Anti-A-O-NH$_2$

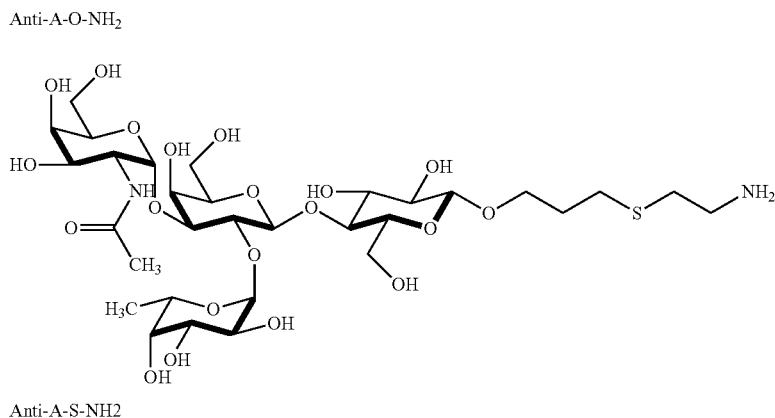

Anti-A-S-NH2

Blood group B antigen tetra-saccharides with linker arm and $NH_2$ functionality:

Scheme 1. The structure of the functional tetraoses used during coupling with Dextran or Cellulose made beads.

Anti-B-O-NH$_2$

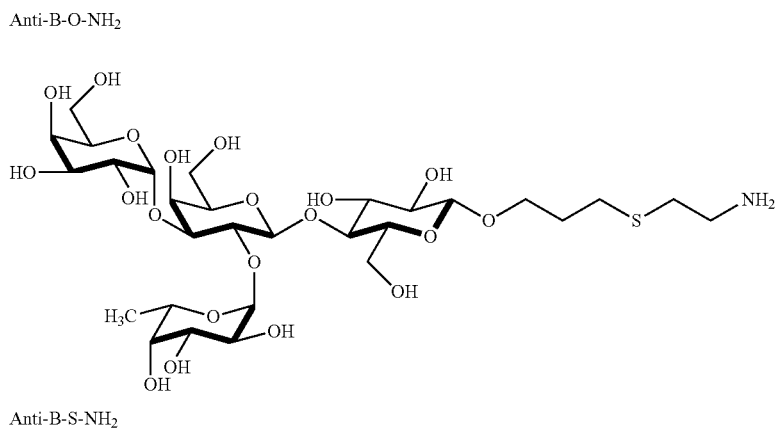

Anti-B-S-NH2

Currently some commercially available products for the reduction of Anti-A and Anti-B Antibodies from human plasma/blood include Glycobar-A and Glycobar-B (Eliciyl, France), Glycosorb-ABO device (Glycorex Transplantation AB, Sweden). Glycosorb® ABO (Glycorex Transplantation, Sweden) and Biosynsorb columns (no longer available) contain the tri-saccharide terminals of the A and B antigens attached to beads were used clinically to reduce anti-A and anti-B antibodies from organs for ABO incompatible transplantation (Genberg 2011). The Glycosorb® ABO device is capable of removing up to 30% of the A/B IgM and 20% A/B IgG levels with a single pass (Kannabhiran 2012). Also, recently filed US patent application US2017/0066839 A1 (Merck Patent GmbH, Germany) describes Anti-A and Anti-B antibody removal based on novel affinity chromatography media.

All above mentioned commercial products are based on natural (cellulose) or synthetic polymer (Polyacrylates) material coupled with appropriate blood group antigen A or blood group antigen B type ligands.

Herein is described functionalization of Crosslinked Dextran or Cellulose based bead functionalization, stabilization and coupling with appropriate tetraose with or without reductive amination method. The representative chemical transformations are summarized in schemes 2, 3 and 4.

In the present invention we disclose the preparation of Dextran or Cellulose based beads (stabilized with secondary crosslinking using multifunctional amines) and its use to immobilize Anti-A and Anti-B tetrasaccharides for subsequent Anti-A and Anti-B Antibody removal from human Plasma or Whole Blood. These examples demonstrate the impact of varying presentations.

Matrix Base: Dextran
Base Polymers:
Commercially available Dextran CL G-50 (100-300 um) from Sigma-Aldrich or In House made Dextran CL (200-600 um)

Scheme 2. Functionalization of Crosslinked dextran-based beads with Blood group A and B tetraose.

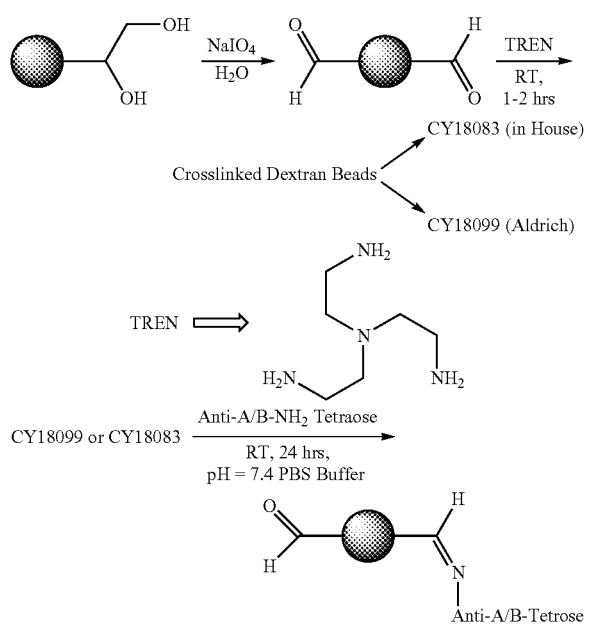

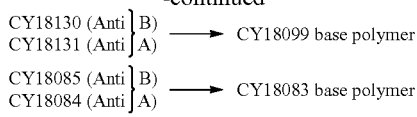

Note: (CY18085 and CY18084 use the Anti-A—O—$NH_2$ and Anti-B—O—$NH_2$ ligands and CY18130 and CY18131 are functionalized with Anti-A—S—$NH_2$ and Anti-B—S—$NH_2$ ligands respectively.)

Crosslinked dextran oxidation followed by secondary crosslinking with minimal amount of any multifunctional primary amines such as Tris-(2-aminoethyl)-amine (TREN) provides beads that are stable under alkaline conditions and capable further coupling with Blood group A and/or B tetraoses. Coupling of the tetraoses containing terminal $NH_2$ groups can be carried without Borohydride based reduction step of imino groups (>C=N—) formed during reaction of crosslinked and oxidized Dextran aldehyde groups and amino containing arm of Blood group A or B tetraoses.

Example 1. Oxidation and Secondary Crosslinking of Crosslinked Dextran Beads: Synthesis of CY18099 Base Polymer Beads (200-600 Um)

Dextran Crosslinked (Aldrich material with bead size: 100-300 um) 50.0 g is suspended in water resulting in a gel formation of approximately 600 mL. This crosslinked dextran hydrogel (600 mL) is treated with $NaIO_4$ (150 g) and 200 mL DI $H_2O$ (1 L glass reactor with mechanical agitator). Reaction time: 2 hours at 25° C. After reaction is complete the formed beads are washed with 5×1 L DI $H_2O$. The yield of resulting hydrogel beads ~400 mL. The oxidized crosslinked dextran beads (400 mL) is treated with 4 mmol (~0.6 g) TREN dissolved in 100 mL DI $H_2O$. Reaction time: 60 minutes at 25° C. After reaction is complete yellowish beads are washed again with 5×500 mL DI $H_2O$ and sieved (200-600 um size). Oxidation and secondary crosslinking with TREN cause dextran beads to expand in volume). The yield of final CY18099 beads ~300 mL (200-600 um).

Example 2. Synthesis of CY18130: Coupling of Blood Group A: Anti-A-S—$NH_2$ Ligand with CY18099

CY18099 polymer beads (5 mL, wet, 200-600 um) Blood Group A tetraose: Anti-A-S—$NH_2$ (15 mg) dissolved in 30 mL pH=7.4 PBS buffer are mixed in 50 mL glass vial. Reaction time: 24 hours at 25° C. After reaction is complete beads are washes with 5×50 mL DI $H_2O$ and finally placed in saline solution. CY18131 polymer beads are synthesized (in a same way as CY18130) by using Blood group B Anti-B-S—$NH_2$).

Matrix Base: Cellulose
Cellulose based beads are made in at least two ways. First by direct oxidation of cellulose powder.

1). Direct oxidation of Cellulose powder suspended in DI water with NaIO4 followed by secondary crosslinking with TREN ligand.

Scheme 3. Functionalization of Crosslinked Cellulose based beads (direct oxidation of cellulose powder) with Blood group A and B tetraose. (Anti-A—O—NH₂ and Anti-B—O—NH₂ ligands)

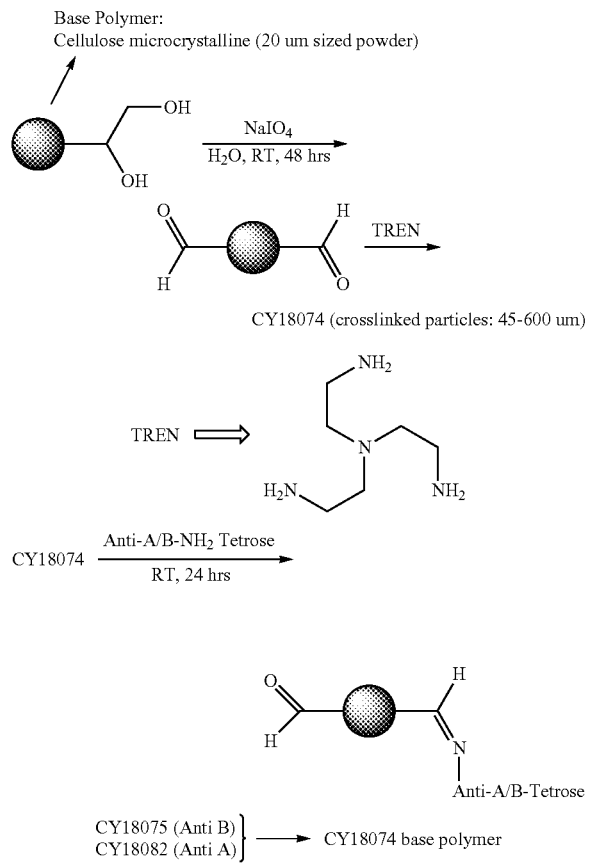

0.02 mmol TREN per 1 ml of wet polymer particles: Partial consumption of aldehyde groups: crosslinking of cellulose particles. Aldehyde content (mmol/mL) in oxidized particles: needs to be determined: Literature values for some oxidation of cellulose powder: at least > 1 mmol/mL wet particles. Sperical bead formation observed after longer oxidation times: 168-240 hrs. Decreasing agitation rate and increasing reaction (oxidation time) seems to produce larger (>100 um) and more spherical beads.

Scheme 4.
Functionalization of Crosslinked Cellulose based beads (prepared using inverse emulsion technique with epichlorohyrine as crosslinker) with Blood group A and B tetraose.
(Anti-A—O—NH₂ and Anti-B—O—NH₂ ligands)

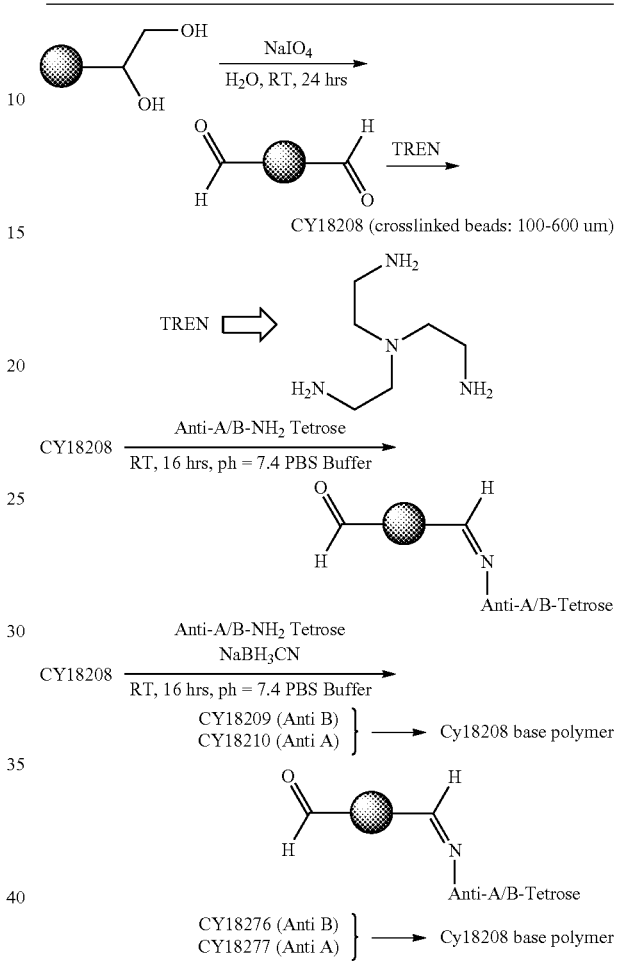

Example 3. Preparation of CY18074 Polymer Beads

Cellulose (microcrystalline, 20 um Powder (Aldrich) is suspended in 200 mL DI water containing 20 g NaIO₄. Bead formation time: 48 hrs. at room temperature. Beads are washed with DI water (5×300 mL) and sieved 45-600 um size. 10 mL of oxidized cellulose beads suspended in 50 mL DI water are reacted with 20 ml TREN solution (0.05 mmol/mL) for 2 hour period at room temperature. Crosslinked beads are washed with DI water (5×100 mL).

2). Cellulose crosslinked beads are made using inverse emulsion technique (with epichlorohydrine as crosslinker) followed by oxidation with NaIO4 and secondary crosslinking with TREN ligand.
Base Polymer:
Cellulose CL Beads Prepared using inverse emulsion (Crosslinked with Epichlorohydrine) (100-600 urn wet particle size).

Example 4. Synthesis of CY18075: Coupling of Blood Group A: Anti-B-S—NH₂ Ligand with CY18074

CY18074 polymer beads (5 mL, wet, 200-600 um) Blood Group B tetraose: Anti-B-S—NH₂ (20 mg) dissolved in 30 mL pH=7.4 PBS buffer are mixed in 50 mL glass vial. Reaction time: 24 hours at 25° C. After reaction is complete beads are washes with 5×50 mL DI H₂O and finally placed in saline solution. CY18082 polymer beads are synthesized (in a same way as CY18075) by using Blood group A: Anti-A-S—NH₂

Example 5. Preparation of CY18208 Cellulose CL Beads

Solution of 40 g NaOH and 16.5 g Thiourea in 200 mL DI water charged in 1 L glass reactor (equipped with mechanical agitator). Cellulose (Aldrich) powder is added. After cellulose is dissolved (at 8° C., 200 rpm, 4 hrs.) Organic Phase (composed of: 100 mL toluene, 170 mL Isooctane, 30 mL Epichlorohydrine and 2.5 g Span 80) is then (at 8° C., 200 rpm) and emulsion is heated up at 70° C. for 16 hrs. After reaction is complete: Organic phase is removed and formed white beads are washed 3×300 mL DI water followed by 2×300 mL Isopropanol wash and finally 2×300 mL DI water wash. Beads are sieved at 100-600 um. Yield ~120 mL (wet). Thus prepared 50 mL of Cellulose CL beads are oxidized with a solution of 15 g $NaIO_4$ in 200 mL DI water (containing 3 drops of conc. $H_2SO_4$, pH ~3.5). Oxidation time: 24 hrs at room temperature. Beads are washed 10×200 mL DI water to remove excess $NaIO_4$ and side products. Yield of oxidized beads: ~30 mL. 30 mL of Oxidized Cellulose CL beads are treated with a solution of TREN in Water (10 mL 0.05 mmol/ml TREN solution) for 1 hour at RT. Yellowish beads are washed with water (DI) yielding ~15 mL CY18208 base polymer containing aldehyde groups.

Example 6. Synthesis of CY18277: Coupling of Blood Group a Tetraose: Anti-A-S—$NH_2$ Ligand with CY18208 Using Reductive Amination Method CY18208 polymer beads (5 mL, wet, 100-600 um) and Blood Group A: Anti-A-S—$NH_2$ ligand (15 mg) dissolved in 20 mL pH=7.4 PBS buffer (containing 3 mg/mL NaBH3CN) are mixed in 50 mL glass vial. Reaction time: 16 hours at 25° C. After reaction is complete beads are washes with 5×50 mL DI $H_2O$ and placed in saline solution. CY18276 Polymer beads are prepared in similar to CY18277 manner using Anti-B-S—$NH_2$ ligand.

Example 7. Use of Polymeric Media to Remove Anti-A and Anti-B Antibodies from Whole Blood Polymers based on dextran or cellulose (beaded form) matrix where also used for removal of Anti-A and Anti-B antibodies from whole blood, Examples include but not limited to the polymers depicted in the scheme 5. These particular polymers are functionalized using oxidation of polysaccharide beads with sodium periodate followed by direct coupling of amino functional blood group A and B tetroses onto the bead surface (no reductive amination or secondary crosslinking is used).
Base Polymer:
Commercially available Dextran CL G-50 (100-300 um)

Scheme 5.
Oxidation of Dextran CL G-50 and attachment of Anti-A—O—$NH_2$ and Anti-B—O—$NH_2$ ligands without using secondary crosslinking and reductive amination method.

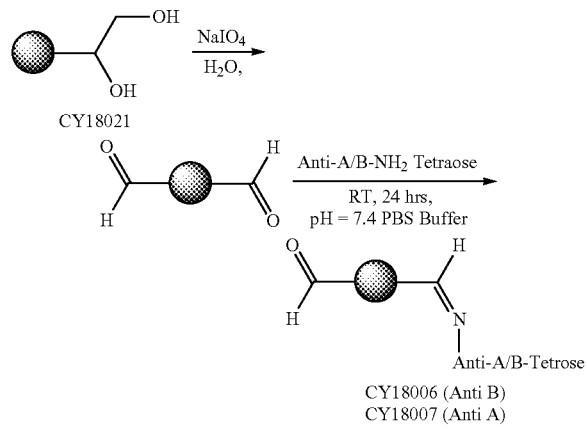

CytoSorbents polymers described in the scheme 2, 3, 4 that showed ≥88% removal [16:1 Plasma:Polymer Ratios] of Blood Group Antibodies:

| Polymer | Functionalization | Antibody (% Reduction) |
|---|---|---|
| CY18083 | Base | 0 |
| CY18084 | A-Ligand | 98 |
| CY18085 | B-Ligand | 97 |
| CY18099 | Base | 0 |
| CY18130 | A-Ligand | 99 |
| CY18131 | B-Ligand | 94 |
| CY18074 | Base | 0 |
| CY18082 | A-Ligand | 94 |
| CY18075 | B-Ligand | 94 |
| CY18208 | Base | 0 |
| CY18210 | A-Ligand | 95 |
| CY18277 | A-Ligand | 97 |
| CY18209 | B-Ligand | 89 |
| CY18276 | B-Ligand | 98 |

CytoSorbents polymers tested using whole blood: CY18006 (B ligand), CY18007 (A Ligand). N=5.

| Polymer | Functionalization | Antibody % Reduction |
|---|---|---|
| CY18007 | A-ligand | 92 |
| CY18006 | B-Ligand | 90 |
| CY18021 | Base | 10 |

Modified Single-Pass Method for Antibody Removal from Blood Using CytoSorbents Polymers:
1. Human whole blood of collected in Citrate-Phosphate-Dextrose and used within 5 days.
2. Bring whole blood to ambient temperature [22-25° C.].
3. Using a 15 ml centrifuge tube, add wet polymers to the 0.5 ml demarcation line. Complete volume to 10 ml using 0.9% saline and invert to wash polymer. Remove saline using a pipette. Add 8 ml of whole blood [16:1 blood:polymer ratio].
4. Invert gently 10 times. Let sit for 60 seconds.
5. Add blood-polymer mixture to a 30 ml cut device with 50 micron polyester filter/rubber 0-ring. Filter blood by gravity flow.
6. Separate plasma from blood via centrifugation. 4000 RPM, 10 mins using the Thermo Scientific Megafuge 16R.
7. Transfer plasma to a new labeled microcentrifuge tube. Determine antibody titer via gel card agglutination assay. The titer of a sample is specified as the lowest dilution with agglutination.

Tube-method procedure for antibody removal from plasma using CytoSorbents polymers:
1. Thaw plasma source in a 37° C. water bath. Remove, dry and place at room temperature until use.
2. Using a 2 ml microcentrifuge tube, add wet polymers to the 0.25 ml demarcation line. Complete volume to 2 ml using 0.9% saline and invert to wash polymer. Remove saline using a pippete and add saline to the 1 ml demarcation line. Serially dilute polymer to 0.625 ml. Remove saline using a pipette. Add 1 ml plasma [16:1 plasma:polymer ratio].
3. Incubate with sharing for 15 minutes at room temperature using the TalBoys Microplate shaker (500 RPM).
4. Separate plasma from blood via centrifugation. 4000 RPM, 10 mins using the Thermo Scientific Megafuge 16R.

5. Transfer plasma to a new labeled microcentrifuge tube. Freeze samples at −80° C. after determining antibody titer.

Polymers tested using plasma: All listed in table above.

Test Procedure for Antibody Titer Determination from plasma treated with Polymers using Ortho Clinical Diagnostics Gel Cards 1. Using glass test tubes, serially dilute plasma using 0.9% saline. Extent of dilutions should be empirically determined for each plasma source.
2. Visually inspect gel cards and confirm foil seal is undamaged. Ensure matrix within each microtube is intact and covered with a layer of liquid. A gentle tapping of the gel-card can re-settle layer of liquid.
3. Label each card with corresponding sample and dilution factor.
4. Gently mix each reagent red blood cell vials until cells are fully suspended. Cells aggregates should not be visible on the bottom of the vial.
5. Add 50 μL of Red Blood cells reagent A or B to microtubes.
6. Add 50 μL of plasma samples and relevant dilutions to relevant microtube.
7. Incubate the gel cards for 15 minutes at 37° C. using the Ortho Workstation.
8. Centrifuge gel cards using the Ortho Workstation Centrifuge at the preset conditions (1032 RPM, 10 mins).
9. Cards are read manually for antibody titer determination. Antibody removal efficiency is calculated as the lowest dilution with agglutination of the reagent red cells Throughout this specification, words are to be afforded their normal meaning, as would be understood by those skilled in the relevant art, unless otherwise indicated. However, so as to avoid misunderstanding, the meanings of certain terms will be specifically defined or clarified.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value.

Where present, all ranges are inclusive and combinable. That is, references to values stated in ranges include every value within that range including the endpoint values.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A and B," "A and C," "B and C," or "A, B, and C."

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other possible embodiment(s) and such a combination is considered to be another embodiment. Conversely, various features of the invention that are, for brevity, described in the context of a single embodiment, may also be provided separately or in any sub-combination. Further, while an embodiment may be described as part of a series of steps or part of a more general structure, each said step or part may also be considered an independent embodiment in itself.

What is claimed:

1. A polymeric media based on modified natural polysaccharides for removing one or both of Anti-A Antibodies and Anti-B Antibodies from human blood or plasma, the media comprising one or both of
   (i) a polymeric solid support comprising a blood group A Antigen ligand attached to the solid support at a ligand loading between 1-5 mg/mL of solid support, and wherein the media is stable under physiological pH conditions, and
   (ii) a polymeric solid support comprising a blood group B Antigen ligand attached to the solid support at a ligand loading between 1-5 mg/mL of solid support, and wherein the media is stable under physiological pH conditions;
   wherein, prior to ligand attachment, each solid support is functionalized with $NaIO_4$ oxidation followed by secondary crosslinking with appropriate di, tri or polyamines; and
   wherein each solid support comprises a beaded form of functional polysaccharide.

2. The polymeric media of claim 1 wherein the blood group A Antigen ligand is a tetrasaccharide.

3. The polymeric media of claim 2 wherein the blood group A Antigen ligand is

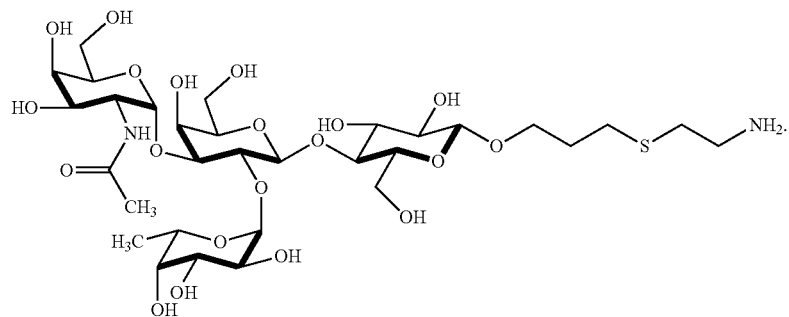

4. The polymeric media of claim 1 wherein the blood group B Antigen ligand is a tetrasaccharide.

5. The polymeric media of claim 4 wherein the blood group B Antigen ligand is

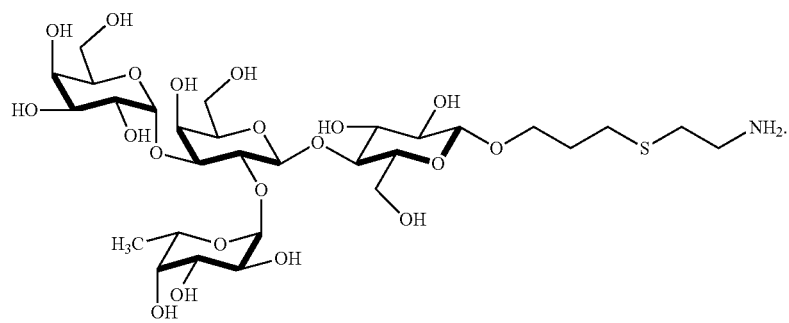

6. The polymeric media of claim 1, comprising both of said blood group A Antigen ligand attached to said solid support and said blood group B Antigen ligand attached to said solid support.

7. The polymeric media of claim 1, wherein each solid support comprises a polymer comprising at least one of cellulose, dextran, starch, agarose, and chitosan.

8. The polymeric media of claim 1, wherein said beaded form of functional polysaccharide with a bead size range of 45-1,000 microns and pore size ranging from non-porous to 1-20,000 angstrom pore diameter.

9. The polymeric media of claim 8, wherein the polysaccharide is functionalized with natural or synthetic compounds selected from peptides, proteins, polysaccharides, lipids and drugs.

10. The polymeric media of claim 1, wherein solid support, are stabilized toward degradation and made stable under wide range of pH (1-14) of the media with partial crosslinking with a di, tri, tetra or polyfunctional primary or secondary amine.

11. The polymeric media of claim 10, wherein the trifunctional amine is tris(2-aminoethyl)amine (TREN).

12. The polymeric media of claim 1, wherein solid support contains partially unreacted aldehyde groups as functional group to be used for coupling of various amino group containing ligands.

\* \* \* \* \*